United States Patent
Bastioli et al.

(10) Patent No.: US 10,030,001 B2
(45) Date of Patent: Jul. 24, 2018

(54) PROCESS FOR THE PRODUCTION AND ISOLATION OF 5-HYDROXYMETHYLFURFURAL

(71) Applicant: Novamont S.P.A., Novara (IT)

(72) Inventors: Catia Bastioli, Novara (IT); Luigi Capuzzi, Novara (IT); Giuseppina Carotenuto, Novara (IT); Anna Di Martino, Novara (IT); Adriano Ferrari, Novara (IT)

(73) Assignee: Novamont S.P.A., Novara (IT)

( * ) Notice: Subject to any disclaimer, the term of this patent is extended or adjusted under 35 U.S.C. 154(b) by 0 days.

(21) Appl. No.: 15/518,861

(22) PCT Filed: Oct. 16, 2015

(86) PCT No.: PCT/EP2015/073991
§ 371 (c)(1),
(2) Date: Apr. 13, 2017

(87) PCT Pub. No.: WO2016/059205
PCT Pub. Date: Apr. 21, 2016

(65) Prior Publication Data
US 2017/0233363 A1 Aug. 17, 2017

(30) Foreign Application Priority Data
Oct. 16, 2014 (IT) .............................. NO2014A0003

(51) Int. Cl.
C07D 307/50 (2006.01)
(52) U.S. Cl.
CPC .................. *C07D 307/50* (2013.01)
(58) Field of Classification Search
CPC .................................................... C07D 307/50
USPC ........................................................ 549/488
See application file for complete search history.

(56) References Cited

U.S. PATENT DOCUMENTS 9,409,877 B2    8/2016    Capuzzi et al.

FOREIGN PATENT DOCUMENTS

| CN | 101811066 A | 8/2010 |
| CN | 101906088 A | 12/2010 |
| WO | WO 2013/066776 A1 | 5/2013 |

OTHER PUBLICATIONS

International Search Report and Written Opinion for PCT/EP2015/073991 dated Dec. 21, 2015.
International Preliminary Report on Patentability (Chapter II) for PCT/EP2015/073991 dated Sep. 9, 2016.
Jadhav et al., Conversion of D-glucose into 5-hydroxymethylfurfural (HMF) using zeolite in [Bmim]Cl or tetrabutylammonium chloride (TBAC)/CrCl$_2$. Tetrahedron Letters. 2012;53(8):983-5.
Yuan et al., Catalytic conversion of glucose to 5-hydroxymethyl furfural using inexpensive co-catalysts and solvents. Carbohydrate Research. Jun. 6, 2011;346(13):2019-23.

*Primary Examiner* — Taofiq A Solola
(74) *Attorney, Agent, or Firm* — Wolf, Greenfield & Sacks, P.C.

(57) ABSTRACT

The present invention relates to a process for the synthesis of 5-hydroxymethyl furfural (HMF) comprising the steps of: 1) dehydrating at least one saccharide selected from monosaccharides having 6 carbon atoms and disaccharides, oligosaccharides or polysaccharides formed from units having 6 carbon atoms or mixtures thereof in the presence of at least one quaternary ammonium salt $R_3R'N^+X^-$; in which: —R, which is the same or different, represents a $C_1$-$C_{16}$ substituted or unsubstituted alkyl group; —R' belongs to the group consisting of: hydrogen, $C_1$-$C_{16}$ substituted or unsubstituted alkyl group, monocyclic substituted or unsubstituted aryl group; —$X^-$ represents an anion selected from chloride, bromide, iodide, fluoride, hydroxide, $BF_4^-$ and $PF_6^-$; at a temperature of between 80 and 120° C., removing water from the reaction medium (dehydration stage) and obtaining a reaction mixture comprising the quaternary ammonium salt, HMF, any unreacted saccharide and having a water content of less than 30% by weight relative to the weight of the product HMF; 2) separating HMF from the said reaction mixture (separation stage).

29 Claims, 1 Drawing Sheet

PROCESS FOR THE PRODUCTION AND ISOLATION OF 5-HYDROXYMETHYLFURFURAL

This application is a U.S. National Stage Application of International Patent Application No. PCT/EP2015/073991, filed Oct. 16, 2015, and entitled "PROCESS FOR THE PRODUCTION AND ISOLATION OF 5-HYDROXYMETHYLFURFURAL," which claims priority under 35 U.S.C. § 119(b) to Italian Patent Application Serial No. NO2104A000003, filed Oct. 16, 2014, each of which is incorporated herein by reference in its entirety for all purposes.

This invention relates to a process for the production and isolation of 5-hydroxymethylfurfural (HMF) from saccharides.

In particular this invention relates to an efficient process whereby 5-hydroxymethylfurfural (HMF) can be produced and isolated from saccharides in high yield and with high purity. HMF is a significantly important product for obtaining a series of useful intermediates, such as 2,5-furandicarboxylic acid, 2,5-dimethylfuran, 2,5-(dihydroxymethyl) furan, etc., from renewable sources.

The most direct synthesis route for obtaining this product is the acid-catalysed dehydration of monosaccharides having 6 carbon atoms such as fructose and glucose, or disaccharides and polysaccharides deriving from these, such as saccharose and inulin, to yield HMF through the elimination of 3 molecules of water per monosaccharide unit:

$$C_6H_{12}O_6 \rightarrow HMF + 3H_2O$$

The conversion may be performed in various types of solvents: water, aprotic dipolar solvents (for example dimethylsulfoxide, N-methyl-2-pyrrolidone, N,N-dimethylformamide, N,N-dimethylacetamide), two-phase systems comprising water and organic solvents (for example 2-butanol, 4-methyl-2-pentanone), ionic liquids (for example N-methyl-2-pyrrolidonium methylsulfonate, 1-ethyl-3-methylimidazolium chloride, 1-butyl-3-methylimidazolium chloride, 1-butyl-3-methylimidazolium tetrafluoroborate).

Various catalyst systems have been used to perform the conversion, such as for example acid catalysts of the mineral acid type, ion exchange resins, zeolites, supported heteropolyacids and metal chlorides (for example $FeCl_3$, $CrCl_2$, $SnCl_4$).

The acidity of the catalysts may however also encourage the rehydration of HMF and its subsequent fragmentation to yield levulinic and formic acids, or its oligomerisation or polymerisation to yield further by-products which contribute to lowering the overall yield of the reaction.

Alkylammonium salts have also recently been proposed as catalysts or solvents for this type of reaction (CN 101906088; CN 101811066; "Tetrahedron Letters", 53, 2012, pages 983-985; "Carbohydrate Research", 346, 2011, pages 2019-2023), with HMF yields varying between 45 and 70% depending upon the starting saccharide.

In any event, even though it is possible to obtain good conversions into HMF with combinations of some of these solvents and catalysts, in particular from fructose, because of the high solubility of HMF in water, its low melting point (30-34° C.) and its relative thermal instability, it is still very difficult to separate it from the reaction medium and by-products, and to obtain it as a high purity isolated product. In fact, HMF yields reported in the literature are generally calculated by analysing reaction mixtures (for example by means of HPLC) and are not determined on the basis of the quantity of product actually isolated and purified.

For example, the use of high boiling point water-soluble solvents, such as dimethylsulfoxide, generally requires separation by fractional distillation and subsequent column chromatography. The use of two-phase water/organic solvent systems, ionic liquids or ammonium salts generally requires laborious extractions with appreciable quantities of organic solvents to separate and recover the product.

Also the process described in Italian application NO2013A000003, which provides higher HMF yields through combining particular alkylammonium salts with specific catalysts, nevertheless requires complex operations for the recovery of HMF, salt and catalyst, and for recycling the solvents used.

Specifically the methods hitherto described in the literature may be used for preparation of the product on a laboratory scale and quantities of the order of a few grams, but are unsuitable for the production of large quantities of HMF on an industrial scale.

It is an object of the present invention to provide an improved process for making 5-hydroxymethylfurfural (HMF).

The applicant has now surprisingly discovered that, through bringing a saccharide at a temperature from 80 to 120° C. in the presence of a quaternary ammonium salt, preferably without the addition of organic solvents, and keeping a low water content during the subsequent HMF synthesis reaction, it is possible to obtain both high yields of HMF, even in the absence of catalyst, while limiting the conversion of HMF into by-products, and at the same time appreciably simplifying the subsequent operations for recovery of the salt and the extraction solvent. The resulting process makes it possible to produce and isolate HMF in high yield with high purity, even on an industrial scale, and is also particularly suitable for continuous operation, with further advantages from the point of view of the economics of the process.

The subject matter of this invention therefore comprises a process for the synthesis of 5-hydroxymethylfurfural (HMF) comprising the steps of:

1) dehydrating at least one saccharide selected from monosaccharides having 6 carbon atoms and disaccharides, oligosaccharides or polysaccharides formed from units having 6 carbon atoms or mixtures thereof in the presence of at least one quaternary ammonium salt $R_3R'N^+X^-$, in which:
    R, which is the same or different, represents a $C_1$-$C_{16}$ substituted or unsubstituted alkyl group;
    R' belongs to the group consisting of: hydrogen, $C_1$-$C_{16}$ substituted or unsubstituted alkyl group, monocyclic substituted or unsubstituted aryl group;
    $X^-$ represents an anion selected from chloride, bromide, iodide, fluoride, hydroxide, $BF_4^-$ and $PF_6^-$;
    at a temperature of between 80 and 120° C. and preferably keeping it stirred for a time of between 1 and 240 minutes, optionally in the presence of an acid catalyst and preferably at a pressure of less than 1 bar (0.1 MPa), removing water from the reaction medium (dehydration stage) and obtaining a reaction mixture comprising the quaternary ammonium salt, HMF, any unreacted saccharide and having a water content of less than 30%, preferably less than 25%, more preferably less than 20%, even more preferably less than 10% by weight relative to the weight of the product HMF;
2) separating HMF from the said reaction mixture (separation stage).

According to a preferred embodiment, the process of the present invention comprises a preliminary step of preheating the saccharide and/or at least one quaternary ammonium salt before the dehydration stage, the dehydration stage being preferably performed at a temperature of between 90 and 120° C.

According to a more preferred embodiment, step 2) of the process of the present invention comprises an extraction of HMF from the reaction mixture in an organic solvent wherein the quaternary ammonium salt and any unreacted saccharide are substantially insoluble, the separation of the resulting liquid phase comprising HMF from the remaining reaction mixture in solid phase and the evaporation and/or distillation of the said organic solvent from HMF.

The process may be carried out either in batch runs or continuously or semi-continuously, preferably continuously.

Herein, step 1) is also referred to as "dehydration stage" and step 2) is also referred to as "separation stage".

The process according to this invention will now be described in greater detail in the following.

Figure 1:
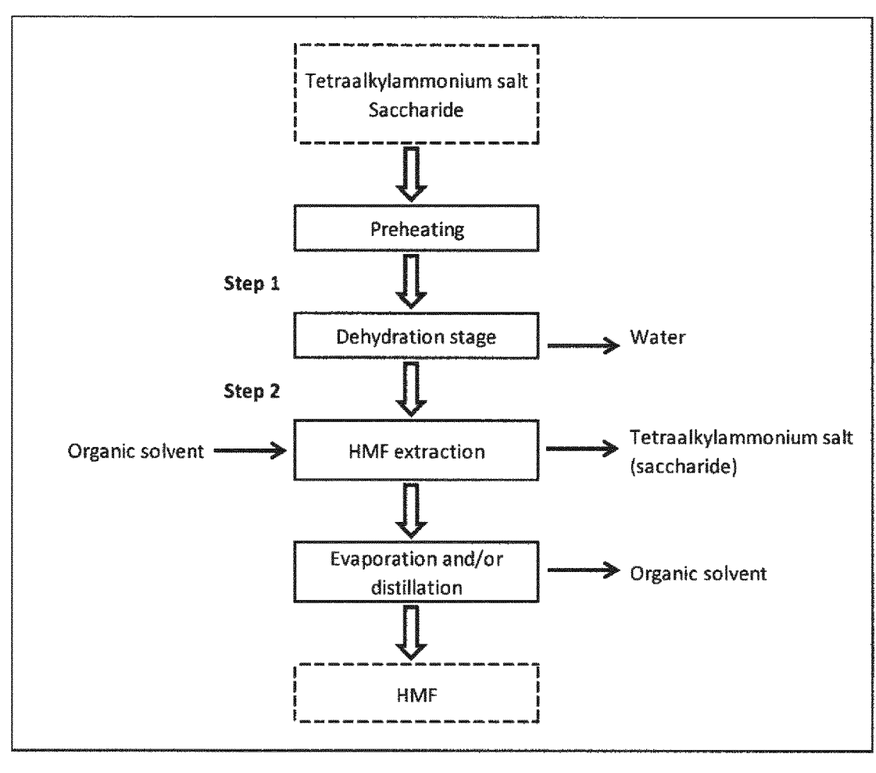
FIG. 1 shows the flow diagram for a preferred embodiment of the process comprising a preheating stage before the dehydration stage and a separation stage comprising the extraction of HMF in an organic solvent.

Saccharides which may be used to obtain HMF through dehydration according to this process are monosaccharides such as fructose, glucose, galactose, mannose, disaccharides such as saccharose, maltose, lactose, cellobiose, oligosaccharides such as oligofructose containing 3-10 fructose units and polysaccharides such as the fructans (e.g. inulin), starch or cellulose.

Specific examples of oligofructose are those having the formula GFn, in which G represents the glucose unit, F the fructose unit and n the number of fructose units, which is between 3 and 10.

Preferred polysaccharides are polysaccharides which are water-soluble at process temperatures, such as for example inulin. Oligosaccharides or polysaccharides which are poorly soluble or insoluble in water may however be used, preferably after preliminary hydrolysis treatment, for example, after acid or enzyme hydrolysis.

The saccharides preferably used in the process according to this invention are selected from fructose, glucose, saccharose, inulin or their mixtures.

A particularly preferred saccharide is fructose. Among the mixtures, the mixtures of saccharides different from each other are preferable, such as those derived from inulin hydrolysis, particularly glucose and fructose mixtures.

As regards the quaternary ammonium salts $R_3R'N^+X^-$ used in the process according to this invention, R is preferably selected from $C_1$-$C_4$ alkyl groups, being the same or different; preferred are methyl groups, ethyl groups, propyl groups, isopropyl groups, butyl groups, isobutyl groups.

R' is preferably selected from hydrogen (H) and $C_1$-$C_{16}$ substituted or unsubstituted, linear or branched alkyl groups; preferred are methyl, ethyl, propyl, isopropyl, butyl, isobutyl, sec-butyl, tert-butyl, benzyl, phenyl, hexyl, octyl, dodecyl, pentadecyl groups.

The possible substituents of R and R' alkyl groups are preferably selected from halogens, carbonyl groups, carboxyl groups, hydroxyl groups, ester groups, $R_2R'N^+$ groups.

$X^-$ preferably represents an halide or hydroxide anion.

One or more quaternary ammonium salts can be used in the process of the present invention. Conveniently used ammonium salts are selected from: tetraalkylammonium salts having fluorinated and non-fluorinated alkyl chains, ammonium salts with asymmetric aliphatic and non-aliphatic groups, bis-quaternary ammonium salts, trialkylammonium salts.

Particularly preferred are tetraalkylammonium salts. Suitable examples are tetraalkylammonium halides or hydroxides preferably having $C_1$-$C_{15}$, and more preferably $C_1$-$C_4$, alkyl groups, optionally substituted by hydroxyl groups. Further preferred tetraalkylammonium salts are chlorides and bromides, such as for example tetramethylammonium chloride, (2-hydroxyethyl) trimethyl-ammonium chloride (choline chloride), tetraethylammonium chloride, tetrapropylammonium chloride, tetramethylammonium bromide, tetraethylammonium bromide, tetrapropylammonium bromide.

A particularly preferred tetraalkylammonium salt is tetraethylammonium bromide.

The ratios by weight between the saccharide and the quaternary ammonium salt which have to be used in the process according to this invention preferably lie between 1:10 and 2:1, more preferably between 1:6 and 1:1, even more preferably between 1:4 and 1:1.

The saccharide and the quaternary ammonium salt can be fed to the dehydration stage in any order and at the same or different temperature, optionally in the presence of water and/or catalyst.

For example, the saccharide and the quaternary ammonium salt may be brought in contact with each other and premixed before being fed to the dehydration stage.

According to an aspect of the invention, the said premixing is carried out at temperatures below the dehydration temperature, preferably comprised between room temperature and 90° C., more preferably between 60 and 90° C., still more preferably between 70 and 90° C. and even more preferably between 80 and 90° C., until obtaining a homogeneous mixture.

According to another aspect, the said pre-mixing is carried out after bringing the saccharide and/or the ammonium salt at a temperature equal to or higher than the reaction temperature, preferably between 80 and 100° C. Advantageously, the premixing is carried out after bringing the salt at a temperature higher than 90° C.

In such a case it is preferable to perform the heating of the ammonium salt at temperatures between 90 and 100° C., advantageously in the presence of quantities of water of between 1 and 50%, preferably of between 2 and 40%, more preferably of between 3 and 30%, even more preferably of between 4 and 20% by weight with respect to the salt, and subsequently to add the saccharide (optionally pre-mixed with a quantity of water sufficient to keep it in solution).

Alternatively, the said saccharide and ammonium salt may be separately fed to the dehydration stage.

In such a case, each is advantageously fed at a temperature equal to the reaction temperature; alternatively one of the two (preferably salt) is preheated to a temperature higher than the reaction while the other is added at a lower temperature.

Both in case of feeding them to the dehydration stage separately, either feeding them pre-mixed with each other, according to a preferred aspect of the invention at least one between the saccharide and the salt is premixed with water before being fed to the dehydration stage. The amount of water present at the time of feeding to the dehydration step is preferably between 10 and 250% by weight with respect to the weight of the saccharide. Said water is advantageously added to the salt and/or the saccharide before their eventual heating.

Advantageously, the process according to the present invention does not require the presence of organic solvents during the reaction of dehydration.

Despite the high melting points of the quaternary ammonium salts and the saccharide, under the operating conditions of the process the reaction mixture is not solid, but is in the form of a fluid, forming a eutectic point at around 70-90° C. This facilitates the transfer of the mixture from a possible pre-heating area and the feeding to the dehydration stage. In the event that the process is carried out continuously, the saccharide and the salt are in fact advantageously premixed and preheated in a reactor separate from that wherein the dehydration step is carried out; the feeding of the preheated fluid mixture to the reactor or reactors of step 1) can therefore be suitably carried out using a common pumping system. In the event that the process is performed in batch mode, the said pre-heating and the dehydration stage are advantageously carried out in the same reactor.

During the dehydration stage, the reaction mixture is preferably kept stirred at a temperature of between 80 and 120° C., preferably 85 and 120° C. and more preferably 90 and 120° C., for a reaction time typically between 1 and 240 minutes. The dehydration reaction is also preferably carried out in an inert environment, for example under nitrogen.

Advantageously the dehydration stage is performed at temperatures between 85 and 110° C., so as to shorten reaction times and avoid the formation of decomposition products associated with high temperatures. When operating in the absence of added catalysts, the temperature is advantageously between 95 and 120° C., more advantageously between 100 and 120° C.

The reaction time also varies according to the operating mode. In the case where the dehydration stage of the process is carried out in batch mode, the reaction time is more preferably between 15 and 120 minutes. In the case where the said step is carried out in continuous mode, the retention time within the reactor or reactors preferably lies between 1 and 120 minutes, and more preferably between 2 and 90 minutes.

The dehydration reaction is preferably performed at a pressure below 1 bar in such a way that any water which may have been fed in (present in the starting mixture) and at least part of the water which forms during the reaction is removed, obtaining a mixture with a water content of less than 30% by weight, preferably less than 25%, more preferably less than 20%, more preferably less than 10% by weight relative to the weight of the product HMF.

According to a particularly advantageous aspect, the water content in the mixture at the end of the dehydration reaction is less than 5% by weight relative to the weight of the mixture, preferably less than 4%, more preferably less than 3%, even more preferably less than 2%.

According to an aspect of the present invention, the dehydration stage is performed in a Continuous Stirred Tank Reactor (CSTR) and the water content of the mixture is preferably kept between 0.01 and 5% by weight throughout the whole duration of the dehydration stage. The water content of the reaction mixture is in fact an important parameter of the process. It must be sufficient to allow the system to be maintained in the fluid state, but not such as to encourage HMF rehydration phenomena during the dehydration step 1, with consequent degradation to levulinic and formic acids.

Also a low water content in the reaction mixture makes it easier to separate the HMF from the quaternary ammonium salt in subsequent separation step.

The water quantity in the reaction mixture can be determined by any method known by the skilled in the art, for example by thermogravimetric analysis (TGA). The thermogravimetric analysis can be performed for example by measuring the weight loss of a 5-10 g sample of the reaction mixture obtained at the end of step 1) at 110° C. until a stable signal is obtained. For the purpose of determining the weight ratio between water and the product HMF in the reaction mixture, the amount of HMF is determined after extraction in organic solvent (2-butanone) of the reaction mixture obtained at the end of the dehydration stage, solvent removal and subsequent gravimetric determination confirmed by HPLC analysis.

Conveniently an initial quantity of water of between 10 and 250% by weight with respect to the saccharide is used, removing as much as possible together with the water formed in the dehydration reaction.

For example, in the case where the saccharide used is fructose, the quantity of water present in the starting mixture is preferably between 10 and 30% by weight, more preferably between 12 and 25% by weight with respect to the fructose. In the case in which the saccharide used is inulin the quantity of water present in the starting mixture is preferably between 25 and 250%, preferably between 30 and 240% by weight with respect to the inulin; in case the inulin is subjected to a preliminary treatment of hydrolysis, obtaining a mixture of fructose and glucose, this quantity is advantageously around 50%.

In accordance with a preferred embodiment, the process is carried out continuously premixing the saccharide and water at a temperature of between 40 and 70° C., more preferably at a temperature of between 55 and 65° C. This operation taking advantage of the increased solubility of saccharides at said temperatures, allows to easily provide a continuous feed of the starting materials to the dehydration step and to reduce the quantity of water used. In the said conditions quantities of water preferably between 10 and 90% by weight with respect to the saccharide are used. Depending upon the nature of the continuous process, mixing of poorly soluble or insoluble polysaccharides with water is advantageously preceded by a preliminary hydrolysis operation, for example using acids or enzymes.

Water can be conveniently removed during the dehydration step by connecting the reactor to a vacuum pump which maintains the internal pressure at the desired value. Preferred pressure values lie between 4 and 900 millibar (0.0004-0.09 MPa). The water removal is favoured for example by operating under nitrogen flow. The water removed in the vapour phase can subsequently be recovered by condensation.

Preferred operating modes during the dehydration step are for example temperatures between 90 and 100° C. and pressures higher than 25 mbar, or temperatures between 100 and 110° C. and pressure higher than 60 mbar, which allow an optimal water removal while minimizing the loss of HMF in the vapour phase.

The water removal can be conveniently carried out gradually, for example, operating a gradual reduction of the pressure, e.g. operating at two or more stages at different pressure values.

By working at high temperatures (e.g. 100-120° C.) during the dehydration stage, it is possible to obtain good conversion of the saccharide to HMF even in the absence of catalyst. When operating in the presence of a suitable acid catalyst reaction temperatures and times are substantially reduced, further limiting the possibilities for degradation of the HMF.

The catalyst may be fed during the dehydration stage or premixed with the quaternary ammonium salt and/or with the saccharide before the dehydration stage. Preferably the catalyst is premixed with water before being fed to the dehydration stage.

The acid catalysts which in principle may be used in the process according to this invention include both Bronsted and Lewis acids. Mineral acids (for example hydrochloric acid, sulfuric acid, phosphoric acid), organic acids (for example oxalic acid, levulinic acid, maleic acid, p-toluenesulfonic acid, methanesulfonic acid), acid ion exchange resins (for example of Amberlyst®, Lewatit® or Diaion® type), zeolites (for example modified with $TiO_2$), heteropolyacids (for example phosphotungstic acid), which may be supported on silica or alumina, metal oxides (for example titanium (IV) oxide, zirconium oxide) possibly supported on silica or alumina, metal halides (for example zinc chloride, aluminium trichloride, ferric chloride, chromium chlorides, boron trifluoride), or metal phosphates (for example zirconium phosphate, titanium phosphate), doped zirconium hydroxide (for example sulphated or tungstated) may therefore be used.

If homogeneous catalysts are used, such as for example the mineral or organic acids listed above, the catalysts will be advantageously separated from the reaction mixture before the HMF separation step 2) (for example by neutralisation and/or filtration on resin).

Catalysts of the heterogeneous type, that is to say those which are not soluble in the reaction media, are particularly preferred. These catalysts are preferably brought in contact with the reaction mixture during the dehydration stage.

Particularly preferred acid catalysts for maximising yields from the dehydration reaction are zirconium phosphate $Zr(HPO_4)_2$, titanium phosphate $Ti(HPO_4)_2$, titanium (IV) oxide $TiO_2$ supported on silica, or phosphotungstic acid $H_3[P(W_3O_{10})_4]$ supported on silica, the latter being more preferred.

According to one aspect of this invention, the dehydration stage of the process is carried out in the presence of an acid catalyst selected from:
 i) titanium (IV) oxide, $TiO_2$, supported on silica having a specific surface area of between 150 and 900 m$^2$/g, calcined at a temperature of between 150 and 900° C.;
 ii) phosphotungstic acid, $H_3[P(W_3O_{10})_4]$, supported on silica having a specific surface area of between 150 and 900 m$^2$/g, calcined at a temperature of between 150 and 900° C.;
 iii) zirconium phosphate, $Zr(HPO_4)_2$;
 iv) titanium phosphate, $Ti(HPO_4)_2$.

Catalysts of type i) may be prepared from silica having the desired specific surface area and a titanium isopropoxide solution in organic solvent (for example dioxane), separating out the catalyst by filtration and calcining it at the desired temperature, as described for example in Inorganica Chimica Acta, 2012, 380, pages 244-251.

Catalysts of type ii) may be prepared by impregnating silica having the desired specific area with a phosphotungstic acid solution in water, and then removing the water at a temperature of between 80 and 200° C. and calcining at the desired temperature.

The specific surface area of catalysts i) and ii) suitable for use in the process according to this invention preferably lies between 100 and 350 m$^2$/g.

The specific surface area may be measured according to the BET method described in S. Brunauer, P. H. Emmett and E. Teller, J. Am. Chem. Soc., 1938, 60, 309, measuring the quantity of gas adsorbed onto the surface of the material.

The specific surface area of mesoporous materials (values between 50 and 400 m$^2$/g) is measured by determining the quantity of nitrogen adsorbed at 77 K and a P/Po of approximately 0.3, and assuming that nitrogen has a transverse cross-sectional area of 16.2 Å$^2$, after the catalyst sample has been degassed at 100° C. overnight under a vacuum of 10$^{-6}$ Torr (approximately 0.13 mPa).

The specific surface area of microporous materials (values between 400 and 1000 m$^2$/g) is measured by determining the quantity of helium adsorbed at 4.2 K and a P/Po of approximately 0.3 and assuming that helium has a transverse cross-sectional area of 1 Å$^2$, after the catalyst sample has been degassed at 100° C. overnight under a vacuum of 10$^{-6}$ Torr (approximately 0.13 mPa).

Catalyst iii) may be prepared as for example reported in Chemistry—A European Journal, 2008, vol. 14, pages 8098.

Catalyst iv) may be prepared as reported for example in Advanced Materials, 1996, 8, pages 291-303, or in Acta Chem. Scand., 1986, A40, pages 507-514.

The quantity of acid catalyst which should be used preferably lies between 0.1 and 20% by weight with respect to the saccharide, preferably between 2 and 10%. In the case of supported catalysts (i-ii) the quantity of active phase (understood to be the chemical species on the inert support which is capable of giving rise to catalytic activity) preferably lies between 0.4 and 10% by weight with respect to the saccharide. In the case of phosphotungstic acid $H_3[P(W_3O_{10})_4]$ supported on silica, the quantity of active phase advantageously lies between 0.5 and 2% by weight with respect to the saccharide.

Because there is limited water content, the mixture comprising the quaternary ammonium salt and the saccharide may be poorly flowing during the dehydration step (for example with viscosity values between 30 and 100 centipoise at 90° C.), which may make it difficult to stir and transfer for performing subsequent operations.

The dehydration reaction is therefore preferably carried out in one or more items of equipment which are suitable for the treatment of high viscosity fluids, such as pastes, gums, plasticine, silicones, adhesives. For example reactors which bring about effective mixing and have suitable heat exchange surfaces and which can apply the vacuum necessary for removing the water will preferably be used.

Specific examples of suitable reactors are horizontal or vertical reactors fitted with rotating blades (for example of the LIST KneaderReactor® type), which guarantee a self-cleaning action for the reactors' internal walls, or reactors provided with a high speed rotor capable of generating a high degree of turbulence (for example reactors for high viscosity technologies developed by Buss-SMS-Canzler, such as thin film evaporators), or reactors fitted with a shaft supporting coaxial discs which mix the fluid encouraging the volatilisation of low boiling point products (for example of the Lurgi Zimmer type), or again reactors provided with one or two stirrers which might be contra-rotating at different speeds. Among those listed above, horizontal reactors are preferred.

The dehydration step can be carried out in one or more reactors, which may be the same or different, which may be placed in series.

Thus according to a further embodiment of this invention, step 1) will be at least partly carried out in one or more cylindrical reactors, preferably horizontal reactors, which may be the same or different, each of which is provided with a stirring system selected from:
 a) rotating blades;
 b) high speed rotors;

c) a shaft supporting coaxial discs;
d) one or more paddle stirrers;
these reactors being optionally connected in series. Type a) reactors, equipped with a stirring system that ensures an efficient mixing, are preferred as they allow to obtain high purity HMF. Those which also allow to reduce the pressure during the dehydration stage, obtaining a final reaction mixture with a water content advantageously equal to or less than 8% by weight, more advantageously equal to or less than 6.5% by weight, relative to the weight of the product HMF are particularly preferred.

According to another aspect of this invention, in the course of the dehydration reaction fresh saccharide, possibly mixed with water in quantities of between 10% and 250% with respect to the weight of the saccharide, are gradually fed in such a way as to keep the saccharide/quaternary ammonium salt ratio in the reactor constant. This allows to further control the effectiveness of the agitation as the reaction progresses.

In step 2) of the process according to this invention HMF is separated from the reaction mixture. Such separation may be performed by techniques known in the art, for example by solvent extraction, distillation, filtration, centrifugation, crystallization or combinations thereof.

According to one aspect of the process, to the reaction mixture obtained at the end of step 1) is added an organic solvent which solubilize the mixture.

The components of the solution can then be separated for example by crystallization, obtaining a solid phase comprising or HMF or the salt together with the saccharide residue. The said solid phase may be separated from the liquid phase by known techniques, for example by filtration. The solvent can then be recovered by distillation and/or evaporation. Alternatively, the solution components can be separated with the aid of semipermeable membranes, for example by means of microfiltration or ultrafiltration.

Examples of suitable organic solvents for the purpose are for example alcohols, water, DMSO, acetonitrile, chloroform, acetone. These solvents favour the cold crystallisation of the salt and allow to maintain HMF in solution, facilitating the separation operations.

According to an advantageous embodiment, the reaction mixture is diluted with an organic solvent in which the quaternary ammonium salt is soluble, generally alcohols. Preferred organic solvents for the dissolution of the mixture are ethyl alcohol, methyl-1-propanol, 1-pentanol, 2-propanol, 3-methylbutan-1-ol, 2-pentanol, allylic alcohol, 1-butanol, 2-methyl-2-propanol, 1-esadecanol. The adding of a solvent or a mixture of organic solvents in which the ammonium salt and the catalyst are both insoluble is then done and these precipitate out as solids which are separated off by filtration. The HMF instead remains dissolved in the organic phase, from which it can easily be recovered by distillation of the solvent or mixture of solvents, preferably at reduced pressure. Preferred organic solvents for precipitation of the quaternary salt and the catalyst (if not already in the solid form) are ethyl acetate, chloroform, tetrahydrofuran (THF), 2-butanone and 4-methyl-2-pentanone, methyl acetate, methyl propyl ether, amyl acetate, iso-amyl acetate, tert-amyl methyl ether, tert-butyl methyl ether.

According to a preferred aspect of the process, to the reaction mixture obtained at the end of the dehydration step is added an organic solvent which solubilize only certain components of the mixture, which may then be separated from the components in the solid form according to techniques known in the field.

According to a particularly advantageous embodiment of the process, the separation of HMF from the reaction mixture during stage 2) is carried out by extracting the HMF in an organic solvent.

By the term "organic solvent" according to the present invention is meant either a single organic solvent or a mixture of organic solvents.

The extraction of HMF in an organic solvent may be carried out according to any of the techniques known to those skilled in the art. For example it is advantageously performed in one or more vessels in series, to which the reaction mixture obtained in step 1) and the organic solvent are fed, preferably counter-currently.

According to a particularly preferred embodiment of the invention, during this step an organic solvent—wherein the salt, the saccharide and advantageously an acid catalyst which may be present are highly insoluble—is added to the reaction mixture comprising the HMF which has been formed by the reaction.

Organic solvents which can conveniently be used in the said embodiment of the process are those in which the solubility of the quaternary ammonium salt is low, generally below 20 g/l at 20° C. (so that the quaternary ammonium salt is substantially insoluble in the solvent) and the solubility of the HMF is high, generally over 100 g/l at 20° C. Preferred examples are esters, ketones, ethers or halogenated alkanes having a boiling point between 65 and 120° C., such as for example ethyl acetate, butyl acetate, isopropyl acetate, 2-butanone, 4-methyl-2-pentanone, tetrahydrofuran, 2-methyltetrahydrofuran. Other examples of solvents that dissolve HMF while leaving undissolved salt are trialkylamines with alkyl groups $C_2$-$C_8$, such as triethylamine, or pelargonic acid. 2-Butanone, ethyl acetate and 4-methyl-2-pentanone are particularly preferred.

According to this aspect of the invention, in a preferred embodiment of the process the separation stage 2) comprises the steps of:
a) adding to the reaction mixture obtained at the end of the dehydration phase an organic solvent or a mixture of organic solvents in which the quaternary ammonium salt and any unreacted saccharide are substantially insoluble, at a temperature comprised between 15° C. and the boiling temperature of the solvent or of the solvent mixture, obtaining a liquid phase comprising the organic solvent or mixture of organic solvents and the HMF, and a solid phase comprising the quaternary ammonium salt and any unreacted saccharide;
b) separating the resulting solid phase from the liquid phase;
c) subjecting the liquid phase thus obtained to crystallization and/or evaporation and/or distillation and separate the organic solvent or mixture of organic solvents from HMF.

According to said embodiment the process optionally includes, before the step 1) of dehydration, a preliminary step of preheating at least one quaternary ammonium salt $R_3R'N^+X^-$ as previously described, preferably a tetraalkylammonium salt, and at least a saccharide selected from monosaccharides having 6 carbon atoms and disaccharides, oligosaccharides or polysaccharides formed from units having 6 carbon atoms or mixtures thereof, obtaining a fluid mixture.

Said fluid mixture is then heated and maintained under stirring during the dehydration step, removing water from the reaction and obtaining a reaction mixture comprising the ammonium salt, HMF and any unreacted saccharide and having a content of water less than or equal to 30% by weight relative to the weight of the product HMF, preferably less than or equal to 5% by weight of the reaction mixture. Said step of dehydration is preferably carried out at a temperature comprised between 90-120° C. and preferably for a time ranging from 1-240 minutes, optionally in the presence of an acid catalyst, and preferably at a pressure less than 1 bar (0.1 MPa).

During the separation stage 2) according to this embodiment, after the addition of the solvent in step a), the mixture is maintained at a temperature typically between 70-90° C. for the time necessary to solubilise the HMF of the reaction mixture in said solvent.

In these operating conditions, a heterogeneous mass is formed in which the quaternary ammonium salt and optionally the unconverted saccharide occur in solid form, while in the liquid phase HMF remains dissolved.

The presence of a water quantity less than 30% by weight relative to the weight of the product HMF, and advantageously less than or equal to 5% in the reaction mixture at the end of the dehydration stage particularly contributes to making the above described separation by extraction more efficient.

The heterogeneous mass obtained after the addition of the solvent in step a) is then subjected, in step b), to a separation of the liquid phase (comprising the organic solvent and the HMF) from the solid phase (comprising the quaternary ammonium salt, optionally the acid catalyst, and possibly the unconverted saccharide).

The said separation of the two phases can be achieved by techniques known to those skilled in the art, for example by decanting, centrifuging or filtration.

Steps a) and b) may be repeated several times, adding new organic solvent to the recovered solid phase in order to maximise the extraction of HMF.

The HMF dissolved in the organic solvent, is then recovered in step c) by crystallization and/or evaporation and/or distillation, for example evaporation and/or distillation.

For example, HMF extracted in the organic solvent may first be crystallized and then separated from the liquid phase by known techniques, for example by filtration and/or centrifugation and/or evaporation of the solvent.

For example, in case 2-butanone is used as solvent, preferred conditions for its evaporation are a temperature of between 70 and 90° C. and a pressure of between 0.1 and 0.5 bar.

According to a preferred aspect of the process, the separation of HMF from the reaction mixture in step 2) of the process comprises one or more operations of evaporation and/or distillation, for example in steam current or reduced pressure, such as molecular distillation. The said operations can be carried out either in order to separate HMF from the reaction mixture after the dehydration step, or to remove any organic solvent from the separated HMF or from the quaternary ammonium salt and the residual saccharide.

These operations are advantageously carried out in one or more evaporators (for example of the thin film or molecular type), preferably operating in vacuo with short residence times. Temperature and pressure conditions which make it possible to remove the solvent or HMF as quickly as possible, avoiding subjecting the HMF to prolonged heating at temperatures very much higher than ambient temperature are preferred.

The distilled off and/or evaporated organic solvent may conveniently be reused in separation step 2) of the process.

The quaternary ammonium salt and the saccharide residue recovered at the end of the separation of step 2), possibly after a purification process to eliminate any solvent residues and HMF, may be reused in step 1) of the process, together with fresh saccharide and the possible addition of salt and water.

This procedure is even more advantageous and preferable in the case where the process operates continuously.

The HMF obtained at the end of the process generally has a degree of purity which is acceptable for any subsequent chemical conversions, for example oxidation to 2,5-furandicarboxylic acid. Alternatively, it may undergo purification processes (for example by crystallisation) where a higher degree of purity is required.

The process according to this invention will now be described by means of non-limiting examples.

EXAMPLES

For the purpose of determining the $H_2O_{residual}$/HMF percent weight ratio, the $H_2O_{residual}$ has been determined by isothermal Thermogravimetric Analysis (TGA), i.e. by measuring the weight loss of a 5-10 g sample of the reaction mixture obtained at the end of the dehydration stage at 110° C. until a stable signal was obtained.

The amount of HMF has been determined after extraction in organic solvent, solvent removal and subsequent gravimetric determination confirmed by HPLC analysis.

A 20-30 g sample of the reaction mixture obtained at the end of step 1) was extracted in 2-butanone (70-80 ml in Examples 1-3; 140-160 ml in Example 4, where the residual water amount is higher) at 70° C. for 2 h. After removal of any traces of the organic solvent by evaporation at a temperature of between 70 and 90° C. and a pressure of between 0.1 and 0.5 bar, the HMF product was weighed.

A sample (1 mg) was dissolved in 1 ml of 0.005N $H_2SO_4$ solution and filtered (filter pore diameter: 0.20 μm) and then analysed by HPLC after calibration using a reference standard in order to determine the purity of HMF.

HPLC analysis have been performed on a chromatograph equipped with RI detector and a Rezex ROA-Organic acid H+ (8%) 300×7.8 mm column. A 0.005N $H_2SO_4$ solution at a flow rate of 0.6 ml/min was used as eluent. The column temperature was set at 65° C.

Catalyst Preparation

A solution of 1.0 g of phosphotungstic acid in 11 ml of distilled water was used to uniformly impregnate 10 g of commercial silica (Aerolyst 3038, Degussa: specific surface area 180 $m^2$/g), to obtain 10% wt HPW/$SiO_2$.

The paste was first dried in a stove at 80° C. for 12 hours and then calcined at 200° C. for 2 hours. A blue/purple colour powder formed; this was then treated at 200° C. for 2 hours and finally for a further 2 hours at 500° C. until a yellow powder was formed.

The 10% wt HPW/$SiO_2$ catalyst so prepared (having a BET specific surface area of 159 $m^2$/g), has been used for the reactions in Examples 2, 3 and 4.

Example 1

Preheating 2.8 kg/min of a quaternary ammonium salt (tetraethylammonioum bromide, TEAB) were continuously fed by means of a gravimetric doser for solids to a stirred vessel having a useful volume of 30 l fitted with a thermostatic jacket. At the same time a solution comprising 85% by weight of fructose and 15% of water, previously heated to 60° C. to keep the sugar in solution, was fed by a pump at a rate of approximately 0.67 kg/min. The mixture containing 81.0% by weight of salt, 16.2% of fructose and 2.8% of water was preheated to 85° C. and then pumped to the reaction apparatus in step 1) after a residence time in the reactor of approximately 10 minutes.

Step 1: Dehydration Stage

The said preheated mixture was fed to a horizontal reactor fitted with rotating blades, having a useful volume of 100 l, at a rate of approximately 3.5 kg/min. The temperature and pressure of the reaction system were held at 100° C. and 450 mbar respectively, removing water from the reactor in the vapour phase. The mean residence time in the reactor was approximately 36 minutes. The departing flow comprised HMF, TEAB, unreacted fructose and a water content of 0.06% by weight, corresponding to a $H_2O_{residual}$/HMF weight ratio of 0.48%.

Step 2: Separation Stage

The flow of products leaving step 1), at a rate of approximately 3.2 kg/min was passed to a second stirred vessel (extractor) having a volume of 70 l, held at a temperature of 70° C., to which 2-butanone was fed at a rate of approximately 1.2 kg/min.

The flow leaving the extractor was collected in the vessel and subsequently filtered to separate out the solid phase containing the salt, TEAB and fructose from the organic solvent containing the extracted HMF.

The HMF is then recovered by evaporation of the 2-butanone from the filtered liquid phase. The evaporation was performed in two steps, the first at 400 mbar and the second at 150 mbar. A yield of approximately 92% of 5-hydroxymethylfurfural having a purity of approximately 95% by weight was obtained.

Example 2

Preheating 6930 g of a quaternary ammonium salt (Tetraethylammonium bromide, TEAB) were fed by means of a gravimetric dispenser for solids to a horizontal stirred reactor having a useful volume of 10 l fitted with a thermostatic jacket. The agitator has two co-rotating blades at a rate of approximately 24/30 min$^{-1}$. In the same reactor 300 g of water were added too. The set point temperature has been regulated to 100° C. The reactor temperature has been increased to 85° C. and after that 1390 g of solid fructose, by using a dispenser for solid, has been charged to the system. The mixture has been heated up to 95° C. The charging operations have been realized under nitrogen flow.

Step 1: Dehydration Stage

At a temperature of 95° C., a slurry consisting of 130 g of heterogeneous catalyst (10% HPW/SiO$_2$) mixed with 250 g of water, has been charged to the reactor. The system has been kept at this temperature and at 1 bar pressure for about 5 minutes more.

At this point the vacuum has been applied until the pressure was 30 mbar, in order to favour the water removing from the reactor to the vapour phase. The reaction time in the reactor, from the charging of catalyst to drying, was approximately of 55 minutes. The product consisted of HMF, TEAB, unreacted fructose and a water content of 6.41 $g_{H2O\ residual}/g_{HMF}$ (%) ($H_2O_{residual}$/HMF percent weight ratio).

Step 2: Separation Stage

The products obtained in step 1 have been discharged from the reactor and passed to a second stirred vessel (extractor) having a volume of 50 l, held at a temperature of 70° C., to which 2-butanone was charged of approximately 20 l.

After mixing for 2 h, the organic phase from the extractor was collected into a vessel and subsequently filtered to separate out the solid phase containing the TEAB and fructose from the organic solvent containing the extracted HMF.

The HMF is then recovered by evaporation of the 2-butanone from the filtered liquid phase. The evaporation was performed at about 65° C. in two steps, the first at 400 mbar and the second at 150 mbar. A yield of approximately 86.6% of 5-hydroxymethylfurfural having a purity of approximately 99% by weight was obtained.

Example 3

Preheating 6930 g of a quaternary ammonium salt (Tetraethylammonium bromide, TEAB) were fed by means of a gravimetric dispenser for solids to a horizontal stirred reactor having a useful volume of 10 l fitted with a thermostatic jacket. The agitator has two co-rotating blades at a rate of approximately 24/30 min$^{-1}$. In the same reactor 300 g of water were added too. The set point temperature has been regulated to 100° C. The reactor temperature has been increased to 85° C. and after that 2780 g of solid fructose, by using a dispenser for solid, has been charged to the system. The mixture has been heated up to 95° C. The charging operations have been realized under nitrogen flow.

Step 1: Dehydration Stage

At a temperature of 94° C., a slurry consisting of 130 g of heterogeneous catalyst (10% HPW/SiO$_2$) mixed with 250 g of water, has been charged to the reactor. The system has been kept at this temperature and at this pressure for about 5 minutes more.

At this point, the vacuum has been applied until 30 mbar to favour the water removing from the reactor to the vapour phase. The reaction time in the reactor, from the charging of catalyst to drying, was approximately of 55 minutes. The product consisted of HMF, TEAB, unreacted fructose and a water content of 5.13 $g_{H2O\ residual}/g_{HMF}$ (%)($H_2O_{residual}$/HMF percent weight ratio).

Step 2: Separation Stage

The products obtained in step 1 have been discharged from the reactor and passed to a second stirred vessel (extractor) having a volume of 50 l, held at a temperature of 70° C., to which 2-butanone was charged of approximately 20 l.

After 2 h mixing, the organic phase from the extractor was collected into a vessel and subsequently filtered to separate out the solid phase containing the TEAB and fructose from the organic solvent containing the extracted HMF.

The HMF is then recovered by evaporation of the 2-butanone from the filtered liquid phase. The evaporation was performed at about 65° C. in two steps, the first at 400 mbar and the second at 150 mbar. A yield of approximately 95.7% of 5-hydroxymethylfurfural having a purity of approximately 99% by weight was obtained.

Example 4

Preheating

A mixture of 2 kg quaternary ammonium salt (TEAB) and 185 g water was added to a vertical stirred reactor having the useful volume of 6 l, equipped with heating jacket, at room temperature. The mixture was heated up to a temperature of 95° C. and 400 g of not-preheated fructose were added. The mixture containing fructose was brought to a temperature of 90° C. and then the catalyst 10% HPW/SiO$_2$ based on phosphotungstic acid supported on silica was added (40 g). The additions of the different components to the reactor were conducted under a nitrogen flow.

Step 1: Dehydration Stage

The dehydration reaction of fructose was conducted for the first 15 minutes at an average temperature of 91° C. and at atmospheric pressure, while in the next 45 minutes the pressure was gradually reduced from 1000 mbar to about 90 mbar. The weight percentage of residual water in the reaction product expressed as H$_2$O$_{residual}$/HMF ratio was 17.1%.

Step 2: Separation Stage

When the reaction was completed the mixture was subjected to the extraction procedure to recover the HMF product. The extraction was carried out using 2-butanone as solvent (about 11 liters) for 2 h at 70° C.

The organic phase containing the HMF extract was separated from the solid phase containing the salt by filtration. The extracted product was recovered by evaporation of the extraction solvent as described in Example 3.

A yield of approximately 71.8% of HMF having a purity of approximately 95.2% by weight was obtained.

In particular, the present invention relates to the following items:

1. Process for the synthesis of 5-hydroxymethylfurfural (HMF) comprising the steps of:
   1) dehydrating at least one saccharide selected from monosaccharides having 6 carbon atoms and disaccharides, oligosaccharides or polysaccharides formed from units having 6 carbon atoms or mixtures thereof in the presence of at least one ammonium salt R$_3$R'N$^+$X$^-$, in which:
      R, which is the same or different, represents a C$_1$-C$_{16}$ substituted or unsubstituted alkyl group;
      R' belongs to the group consisting of: hydrogen, C$_1$-C$_{16}$ substituted or unsubstituted alkyl group, monocyclic substituted or unsubstituted aryl group;
      X$^-$ represents an anion selected from chloride, bromide, iodide, fluoride, hydroxide, BF$_4^-$ and PF$_6^-$;
      at a temperature of between 80 and 120° C. (preferably 90 to 120° C.) removing water from the reaction medium (dehydration stage) and obtaining a reaction mixture comprising the quaternary ammonium salt, HMF, any unreacted saccharide and having a water content of less than 30% by weight relative to the weight of the product HMF;
   2) separating HMF from the said reaction mixture (separation stage).

2. Process according to item 1 further comprising a preliminary step of preheating the saccharide and/or the quaternary ammonium salt before the dehydration stage, preferably preheating a mixture of saccharide and at least one quaternary ammonium salt to obtain a fluid mixture.

3. Process according any of items 1 to 2 wherein the saccharide and the quaternary ammonium salt are brought in contact with each other and premixed before being fed to the dehydration stage.

4. Process according any of items 1 to 3 wherein the saccharide and the quaternary ammonium salt are separately fed to the dehydration stage.

5. Process according any of items 1 to 4 wherein at least one of the saccharide and the quaternary ammonium salt is premixed with water before being fed to the dehydration stage.

6. Process according to any of items 1 to 5 wherein water is fed to the dehydration stage in an amount between 10 and 250% by weight with respect to the weight of the saccharide.

7. Process according any of items 1 to 6 wherein the reaction time of the dehydration stage is between 1 and 240 minutes.

8. Process according any of items 1 to 7 wherein the dehydration stage is performed at temperatures between 85 and 110° C.

9. Process according to any one of items 1 to 8 wherein the dehydration stage is performed at a pressure below 1 bar.

10. Process according to any one of items 1 to 9 wherein the saccharide in dehydration stage is selected from fructose, glucose, saccharose, and inulin or mixtures thereof.

11. Process according to any one of items 1 to 10 wherein the weight ratio between the saccharide and the quaternary ammonium salt fed in the dehydration stage is between 1:10 and 2:1, preferably 1:10 and 1:1, more preferably 1:6 and 1:1 and most preferably 1:4 and 1:1.

12. Process according to item 11 wherein fresh saccharide is gradually fed during the dehydration stage to keep the saccharide/quaternary ammonium salt ratio constant in the reactor.

13. Process according to any of items 1 to 12 wherein the said quaternary ammonium salt is selected from tetraalkylammonium salts having fluorinated and non-fluorinated alkyl chains, tetraalkylammonium salts having hydroxylated or non-hydroxylated alkyl chains, ammonium salts with asymmetric aliphatic and non-aliphatic groups, bis-quaternary ammonium salts, and trialkylammonium salts.

14. Process according to item 13 wherein the said quaternary ammonium salt is a tetraalkylammonium salt.

15. Process according to item 14 wherein the tetraalkylammonium salt is a tetraalkylammonium halide or hydroxide having hydroxylated or non-hydroxylated C$_1$-C$_{15}$ alkyl groups.

16. Process according to any of items 1 to 15 wherein an acid catalyst is fed during the dehydration stage or premixed with the quaternary ammonium salt and/or the saccharide before the dehydration stage.

17. Process according to any of items 1 to 16 wherein the dehydration stage is performed in the presence of an acid catalyst selected from:
   i) titanium (IV) oxide, TiO$_2$, supported on silica having a specific surface area of between 150 and 900 m$^2$/g, calcined at a temperature of between 150 and 900° C.;
   ii) phosphotungstic acid, H$_3$[P(W$_3$O$_{10}$)$_4$], supported on silica having a specific surface area of between 150 and 900 m$^2$/g, calcined at a temperature of between 150 and 900° C.;

iii) zirconium phosphate, $Zr(HPO_4)_2$;
iv) titanium phosphate, $Ti(HPO_4)_2$.

18. Process according to any one of items 1 to 17 wherein the dehydration stage is at least partially performed in one or more cylindrical reactors, equal or different among them, each of which equipped with a stirring system selected from:
   a) rotating blades;
   b) high-speed rotor;
   c) coaxial disks fitted on a shaft;
   d) one or more paddle stirrers.

19. Process according to any of items 1 to 18 wherein the water content at the end of the dehydration stage is less than 5% by weight relative to the weight of the reaction mixture.

20. Process according to any of items 1 to 19 wherein the water content of the reaction mixture obtained in the dehydration stage is less than 20% by weight relative to the weight of the product HMF.

21. Process according to item 20 wherein the water content of the reaction mixture obtained in the dehydration stage is less than 10% by weight relative to the weight of the product HMF.

22. Process according to any of items 1 to 21 wherein the separation stage 2) comprises the steps of:
   a) adding to the reaction mixture obtained at the end of the dehydration stage an organic solvent or a mixture of organic solvents in which the quaternary ammonium salt and any unreacted saccharide are substantially insoluble, at a temperature between 15° C. and the boiling temperature of the solvent or of the solvent mixture, obtaining a liquid phase comprising the organic solvent or mixture of organic solvents and the HMF, and a solid phase comprising the quaternary ammonium salt and any unreacted saccharide;
   b) separating the resulting solid phase from the liquid phase;
   c) subjecting the liquid phase thus obtained to crystallization and/or evaporation and/or distillation and separate the organic solvent or mixture of organic solvents from HMF.

23. Process according to item 22 wherein the organic solvent of step a) is selected from esters, ketones, ethers or halogenated alkanes having a boiling point between 65 and 120° C.

24. Process according to any one of items 22 to 23 wherein the separation of the liquid phase from the solid phase of step b) is performed by decantation, filtration or centrifugation.

25. Process according to any one of items 22 to 24 wherein the steps a) and b) are repeated several times.

26. Process according to any one of items 1 to 25 wherein the separation stage 2) comprises one or more operations of evaporation and/or distillation.

27. Process according to any one of items 1 to 21 wherein HMF is separated from the reaction mixture after the dehydration step by evaporation or distillation.

28. Process according to any one of items 1 to 27 wherein the quaternary ammonium salt and the saccharide residue recovered at the end of the separation stage 2) are reused in the dehydration stage of the process.

29. Process according to any one of items 1 to 28 performed continuously.

The invention claimed is:

1. Process for the synthesis of 5-hydroxymethylfurfural (HMF) comprising the steps of:
   1) dehydrating at least one saccharide selected from monosaccharides having 6 carbon atoms and disaccharides, oligosaccharides or polysaccharides formed from units having 6 carbon atoms or mixtures thereof in the presence of at least one quaternary ammonium salt $R_3R'N^+X^-$, in which:
      R, which is the same or different, represents a $C_1$-$C_{16}$ substituted or unsubstituted alkyl group;
      R' belongs to the group consisting of: hydrogen, $C_1$-$C_{16}$ substituted or unsubstituted alkyl group, monocyclic substituted or unsubstituted aryl group;
      $X^-$ represents an anion selected from chloride, bromide, iodide, fluoride, hydroxide, $BF_4^-$ and $PF_6^-$;
   at a temperature of between 80 and 120° C., removing water from the reaction medium (dehydration stage) and obtaining a reaction mixture comprising the quaternary ammonium salt, HMF, any unreacted saccharide and having a water content of less than 30% by weight relative to the weight of the product HMF;
   2) separating HMF from the said reaction mixture (separation stage).

2. Process according to claim 1 further comprising a preliminary step of preheating the said saccharide and/or the quaternary ammonium salt before the dehydration stage.

3. Process according to claim 1 wherein the saccharide and the quaternary ammonium salt are brought in contact with each other and premixed before being fed to the dehydration stage.

4. Process according to claim 1 wherein the saccharide and the quaternary ammonium salt are separately fed to the dehydration stage.

5. Process according to claim 1 wherein at least one of the saccharide and the quaternary ammonium salt is premixed with water before being fed to the dehydration stage.

6. Process according to claim 1 wherein water is fed to the dehydration stage in an amount between 10 and 250% by weight with respect to the weight of the saccharide.

7. Process according to claim 1 wherein a reaction time of the dehydration stage is between 1 and 240 minutes.

8. Process according to claim 1 wherein the dehydration stage is performed at temperatures between 85 and 110° C.

9. Process according to claim 1 wherein the dehydration stage is performed at a pressure below 1 bar.

10. Process according to claim 1 wherein the saccharide in the dehydration stage is selected from fructose, glucose, saccharose, and inulin or mixtures thereof.

11. Process according to claim 1 wherein a weight ratio between the saccharide and the quaternary ammonium salt fed in the dehydration stage is between 1:10 and 2:1.

12. Process according to claim 11 wherein fresh saccharide is gradually fed during the dehydration stage to keep the saccharide/quaternary ammonium salt ratio constant in a reactor in which the dehydration stage occurs.

13. Process according to claim 1 wherein the quaternary ammonium salt is selected from tetraalkylammonium salts having fluorinated and non-fluorinated alkyl chains, tetraalkylammonium salts having hydroxylated or non-hydroxylated alkyl chains, ammonium salts with asymmetric aliphatic and non-aliphatic groups, bis-quaternary ammonium salts, and trialkylammonium salts.

14. Process according to claim 13 wherein the quaternary ammonium salt is a tetraalkylammonium salt.

15. Process according to claim 14 wherein the tetraalkylammonium salt is a tetraalkylammonium halide or hydroxide having hydroxylated or non-hydroxylated $C_1$-$C_{15}$ alkyl groups.

16. Process according to claim 1 wherein an acid catalyst is fed during the dehydration stage or premixed with the quaternary ammonium salt and/or the saccharide before the dehydration stage.

17. Process according to claim 1 wherein the dehydration stage is performed in the presence of an acid catalyst selected from:
   i) titanium (IV) oxide, $TiO_2$, supported on silica having a specific surface area of between 150 and 900 m$^2$/g, calcined at a temperature of between 150 and 900° C.;
   ii) phosphotungstic acid, $H_3[P(W_3O_{10})_4]$, supported on silica having a specific surface area of between 150 and 900 m$^2$/g, calcined at a temperature of between 150 and 900° C.;
   iii) zirconium phosphate, $Zr(HPO_4)_2$;
   iv) titanium phosphate, $Ti(HPO_4)_2$.

18. Process according to claim 1 wherein the dehydration stage is at least partially performed in one or more cylindrical reactors, equal or different among them, each of which is equipped with a stirring system selected from:
   a) rotating blades;
   b) high-speed rotor;
   c) coaxial disks fitted on a shaft;
   d) one or more paddle stirrers.

19. Process according to claim 1 wherein the water content at the end of the dehydration stage is less than 5% by weight relative to the weight of the reaction mixture.

20. Process according to claim 1 wherein the water content of the reaction mixture obtained in the dehydration stage is less than 20% by weight relative to the weight of the product HMF.

21. Process according to claim 20 wherein the water content of the reaction mixture obtained in the dehydration stage is less than 10% by weight relative to the weight of the product HMF.

22. Process according to claim 1 wherein the separation stage 2) comprises the steps of:
   a) adding to the reaction mixture obtained at the end of the dehydration stage an organic solvent or a mixture of organic solvents in which the quaternary ammonium salt and any unreacted saccharide are substantially insoluble, at a temperature between 15° C. and the boiling temperature of the solvent or of the solvent mixture, obtaining a liquid phase comprising the organic solvent or mixture of organic solvents and the HMF, and a solid phase comprising the quaternary ammonium salt and any unreacted saccharide;
   b) separating the resulting solid phase from the liquid phase;
   c) subjecting the liquid phase thus obtained to crystallization and/or evaporation and/or distillation to separate the organic solvent or mixture of organic solvents from HMF.

23. Process according to claim 22 wherein the organic solvent of step a) is selected from esters, ketones, ethers or halogenated alkanes having a boiling point between 65 and 120° C.

24. Process according to claim 22 wherein separating the resulting solid phase from the liquid phase in step b) is performed by decantation, filtration or centrifugation.

25. Process according to claim 22 wherein the steps a) and b) are repeated several times.

26. Process according to claim 1 wherein the separation stage 2) comprises one or more operations of evaporation and/or distillation.

27. Process according to claim 1 wherein HMF is separated from the reaction mixture after the dehydration step by evaporation or distillation.

28. Process according to claim 1 wherein the quaternary ammonium salt and the unreacted saccharide recovered at the end of the separation stage 2) are reused in the dehydrating step 1) of the process.

29. Process according to claim 1 wherein the process is performed continuously.

* * * * *